United States Patent [19]
Richardt et al.

[11] Patent Number: 5,811,607
[45] Date of Patent: Sep. 22, 1998

[54] COMPOSITE SHINGLE PARTICLE SALVAGE SYSTEM

[76] Inventors: Anthony D. Richardt, 404 Old Cannon Way, Evansville, Ind. 47711; Ervin W. Savage, 4420 Kratzville Rd., Evansville, Ind. 47710; Keith Moore, 4001 E. Blackford Rd., Mt. Vernon, Ind. 47620; Kent Moore, 852 S. Alvord Blvd., Evansville, Ind. 47714

[21] Appl. No.: 629,432

[22] Filed: Apr. 9, 1996

Related U.S. Application Data

[63] Continuation-in-part of Ser. No. 354,581, Dec. 12, 1994, abandoned.
[51] Int. Cl.$^6$ .............................. C07C 7/10; C07C 1/00; C10C 1/00; B01D 11/00
[52] U.S. Cl. .................. 585/241; 585/240; 585/833; 585/867; 208/22; 208/45; 208/435; 196/14.52; 196/100; 422/261; 422/280; 422/281; 422/285; 422/292
[58] Field of Search ...................... 585/241, 240, 585/833, 867; 208/22, 44, 45, 400, 39, 428, 435; 196/14.52, 100; 422/261, 280, 281, 285, 292, 298

[56] References Cited

U.S. PATENT DOCUMENTS

| 4,222,851 | 9/1980 | Good et al. ............................... 208/45 |
| 5,337,965 | 8/1994 | Chiovitti ................................... 241/19 |
| 5,417,864 | 5/1995 | Varadarej ................................. 210/703 |

*Primary Examiner*—Bekir L. Yildirim
*Attorney, Agent, or Firm*—Ladas & Parry

[57] ABSTRACT

A process and apparatus for the recovery of hydrocarbons from hydrocarbon containing composite materials, particularly roofing materials including asphalt and solid components to recover asphalt and the solid components. The process includes the steps of: agitating the materials with a solvent, preferably a terpene, to form a hydrocarbon/solvent mixture; heating the hydrocarbon/solvent mixture to vaporize the solvent; recovering the hydrocarbons; and recovering the solvent as a liquid by condensing the solvent vapor. The apparatus includes a composite materials washer for holding the composite materials and a solvent; means for agitating the composite materials washer to dissolve the hydrocarbons in the solvent; and a separator for vaporizing the solvent in the hydrocarbon/solvent mixture and recovering the hydrocarbons.

22 Claims, 2 Drawing Sheets

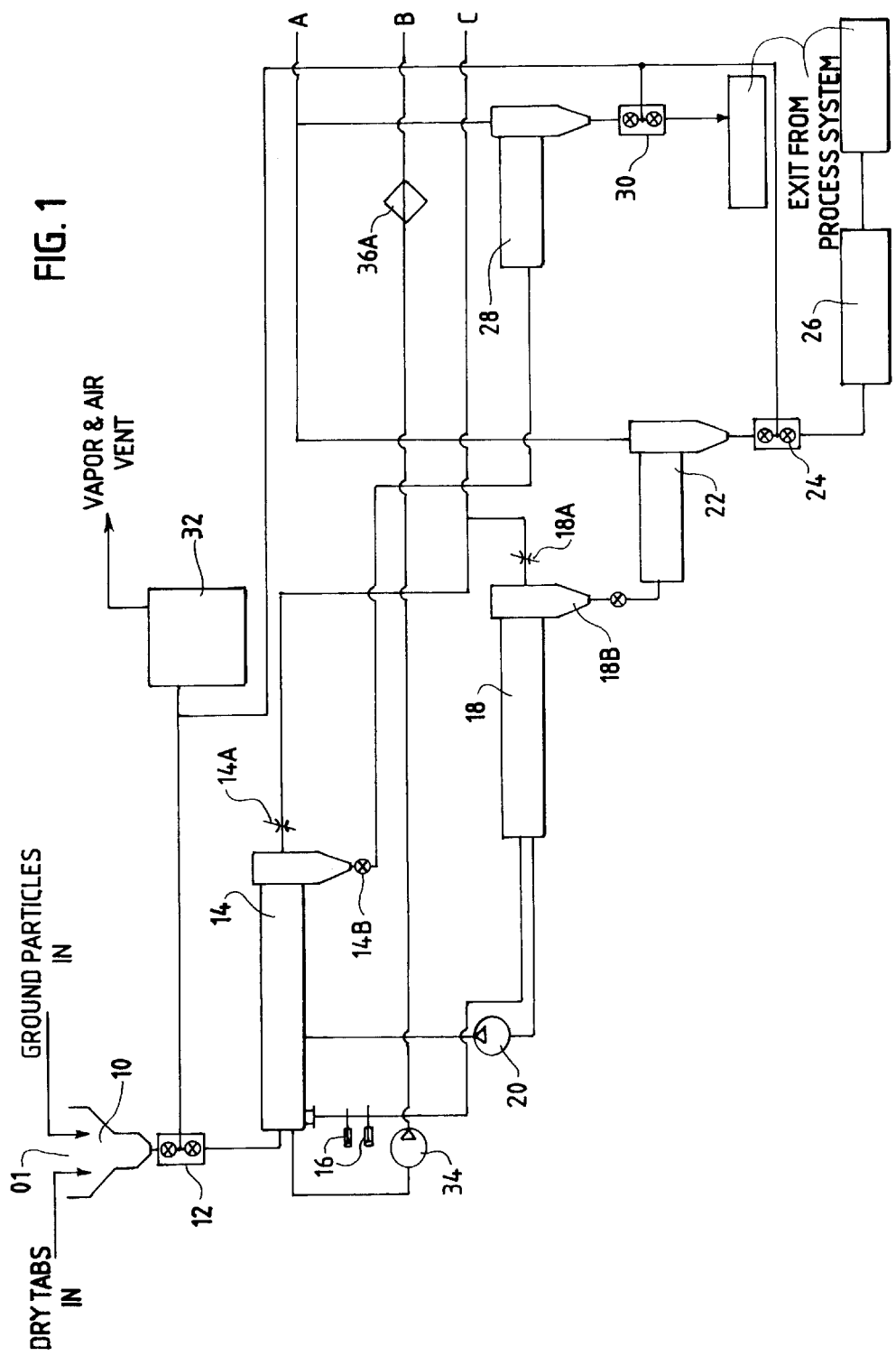

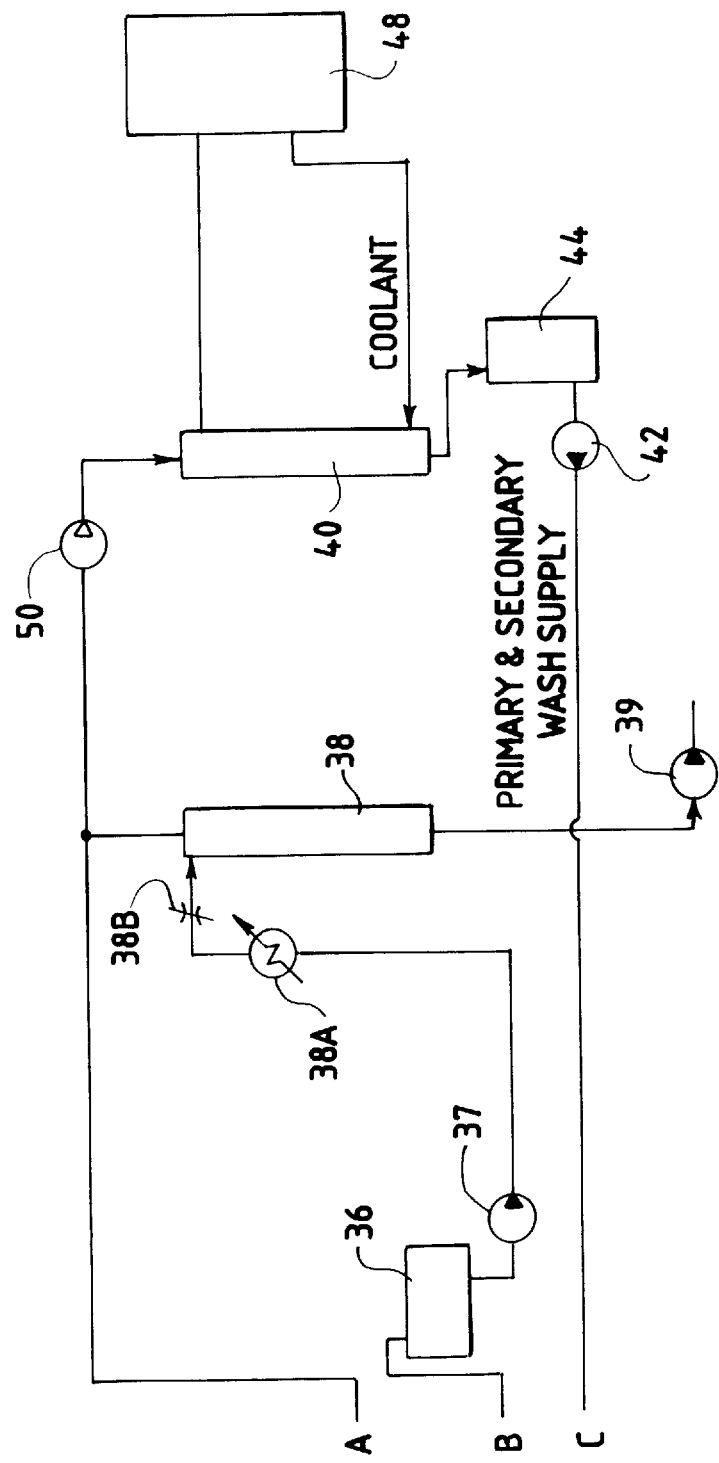

COMPOSITE SHINGLE PARTICLE SALVAGE SYSTEM

The present application is a continuation in part of application Ser. No. 08/354,581, filed Dec. 12, 1994, abandoned.

BACKGROUND OF THE INVENTION

1. Field of the Invention

The present invention relates to an improved process and apparatus for recycling composite materials with a hydrocarbon binder, especially roofing materials including asphalt, felt (glass fiber or organic), and granular materials, such as roof shingles and roof shingle tabs produced as a by-product in an asphalt roofing shingle manufacturing process.

2. Description of the Related Art

Suitable disposal of materials containing asphalt is becoming more difficult. The increasing cost of landfills and the decreasing availability of landfill sites are making land disposal of asphalt containing materials less and less attractive. Incorporation of the byproducts of asphalt shingle manufacturing, such as tabs and damaged shingles, into the materials used in road bed and road surfacing is becoming increasingly difficult as other industries such as tire, glass and reprocessed road materials are competing for the same application. In the foreseeable future, disposal of composite materials containing hydrocarbons or hydrocarbon derivatives including plastics and rubber may also become increasingly difficult.

Asphalt roofing material manufacturers need a simple and cost effective way to reclaim and recycle their production scrap. Roofing contractors also need a simple and cost effective alternative to landfills for their roofing material refuse.

Methods have been proposed to separate the components of roofing material refuse for applications utilizing the individual components. All methods to date to separate and recycle roofing material composites are complicated and expensive, employ undesirable solvents or both.

U.S. Pat. No. 4,222,851 to Good discloses a process and apparatus for the recovery of asphalt shingle components by solvent extraction. The apparatus in Good includes: a hammer mill for shredding asphalt shingle and roofing wastes (ASRW); an extractor-desolventizer drum (contact zone) for successively washing the shredded wastes with petroleum distillate solvents of increasing concentration to dissolve the asphalt; a plurality of tanks for storing the solvents and the solvent/asphalt mixture removed from the extractor-desolventizer after each washing; evaporator & flash tanks for vaporizing the solvent in the solvent/asphalt mixture to obtain an asphalt fraction of 90 to 95%; and an asphalt stripping column for contacting the concentrated asphalt with steam under vacuum to remove any residual solvent.

In operation, the apparatus in Good processes the asphalt shingle and roofing wastes in the following sequence. The wastes are introduced into the hammer mill and shredded into pieces smaller than about 3"×3". A solid feed inlet of the extractor-desolventizer drum is then opened to permit the shredded waste to be introduced into the extractor-desolventizer drum. A contacting miscella from a first storage tank is introduced into the extractor-desolventizer and the drum is rotated to contact the solids and liquid in order to extract a portion of the asphalt from the shredded wastes. The drum is stopped and the miscella is passed to a strong miscella storage tank through a fluid communication line. A second contacting miscella of increased concentration is introduced into the drum and agitated with the solids in a similar manner. The miscella from the second washing is passed to a storage tank through a fluid communication line. A third contacting miscella, essentially pure solvent, is then introduced into the drum and agitated with the solids. The miscella from the third washing is also passed to a storage tank. After the third washing, steam is introduced into the extractor-desolventizer to vaporize the residual solvent in the solid material remaining after the three washings. A steam-solvent stream is then withdrawn to a condenser. The remaining solids are discharged from the drum and passed to a screen classifier, wherein the solids are separated into filler and granules.

The concentrated asphalt/solvent miscella from the strong miscella storage tank is passed through a heat exchanger to raise the miscella to its boiling point and introduced into a first stage and a second stage recirculating-type evaporator wherein the solvent is vaporized to obtain an asphalt fraction containing from 90 to 95% asphalt. The concentrated asphalt is then passed to the upper portion of the asphalt stripping column wherein the concentrated asphalt is contacted in counter-current direct contact with steam to remove any residual solvent. The asphalt stripping operation yields a commercial grade substantially solvent-free asphalt which is withdrawn from the asphalt stripping column. Therefore, the process in Good is capable of treating waste asphalt shingles to recover, in reusable form, the solid components and the asphalt.

U.S. Pat. No. 5,337,965 to Chiovitti discloses another method and apparatus for recycling asphalt based roofing material which typically comprises a body of asphalt and fiber, with aggregate on and adhered to the asphalt. The aggregate is separated from the asphalt body without substantially reducing the size of the aggregate by causing the asphalt bodies with aggregate to impact each other. The disengagement of the aggregate from the asphalt body may be achieved by placing asphalt bodies with aggregate in water to form a slurry, which is agitated. The asphalt bodies float to the top of the liquid, which is a non-solvent for asphalt, and are removed while the aggregate of undiminished size is separately recovered.

Good, while providing suitable means for recovery of asphalt and solid components from roofing materials, has drawbacks. Initial grinding treatment of the asphalt containing material is disclosed. A 3-cycle wash utilizing solvents of increasing concentrations and subsequent storage and evaporation treatment of miscellas is necessitated by the process. Extensive special process equipment for handling the solvents of different concentrations is also necessary. Steaming treatment of the extractor-desolventizer to vaporize any residual solvent remaining in the solid material after the third solvent washing is also disclosed as a necessary part of the process. During vaporization of the residual solvent from the solids, a steam-solvent stream must be withdrawn from the extractor-desolventizer and passed to a condenser. The introduction of steam into the process creates a number of problems. First, the extractor-desolventizer is purged with steam between cycles causing the solvent system to become contaminated with steam condensate. Second, the vent or vapor header is laden with steam causing the need for several pumps, heat exchangers and process vessels to separate the steam condensate from the solvent. Third, an additional step is required to remove the moisture from the product.

The use of hazardous, toxic, flammable, or otherwise environmentally undesirable solvents in the asphalt extraction step is yet another drawback of this reference. For example, Good discloses the use of commercial petroleum distillate solvents, such as those containing heptane and toluene in the asphalt recovery process. Both heptane and toluene are widely recognized as being flammable. toxic, and creating many risks in use. With the increasing environmental regulation of the use, treatment, storage, and disposal of hazardous wastes, the use of solvents, such as toluene and heptane present environmental problems for the users of processes employing these solvents. Pollution control efforts required to limit solvent losses and harmful emissions to the atmosphere present serious cost and other efficiency concerns. Additionally, extensive process equipment required to re-refine solvents greatly increase the cost of the asphalt shingle component recovery apparatus. Another drawback in using light end petroleum distillates, such as heptane is that they lower the penetration value and softening point of the asphalt recovered in the solvent extraction process.

The method and apparatus disclosed in Chiovitti also has disadvantages. The primary drawback of the Chiovitti apparatus is the introduction of water into the process. As a result, the apparatus operates as a batch unit that requires the drying of the recovered solid materials in a separate step. Therefore, the production efficiencies of a continuous closed system process cannot be obtained in the method and apparatus disclosed in Chiovitti.

Consequently, there is a need in the art for an improved process and apparatus for recovering asphalt and solid components from waste asphalt shingles and the like that provides a cost effective, continuous, environmentally friendly, economically feasible alternative to processes known in the art.

The present invention fulfills these needs and more by providing a cost effective process and apparatus for the recovery of asphalt and solid components from waste asphalt shingles in a continuous system without the need for preparatory measures such as the preliminary grinding of the waste materials, multiple material washing steps, or the introduction of water into the system.

Another object of the present invention is to provide a process and an apparatus for recovering the asphalt and solid components from waste asphalt shingles that use environmentally safe solvents that do not adversely affect the recovered asphalt, do not require extensive solvent recovery equipment, and do not require special handling procedures.

A further object of the present invention is to provide a process and an apparatus for the recovery of asphalt and solid components from waste asphalt shingles in a closed system below atmospheric pressure to prevent loss of solvent and maintain the quality of the environment around the system.

The process and apparatus of the present invention overcome the problems in the art by way of an apparatus that operates continuously, using a non-hazardous, non-toxic, nonflammable, and biodegradable terpene solvent. Unground, dry material is introduced into the process and apparatus for processing and the process and apparatus are maintained as devoid of water as possible throughout the process in order to eliminate the need for extensive solvent recovery equipment, hereinafter meaning equipment for the separation of a solvent/water mixture. The apparatus operates as a closed system below atmospheric pressure to prevent loss of solvent and harmful emissions to the environment.

SUMMARY OF THE INVENTION

According to the present invention, the foregoing and other objects and advantages are attained by a continuous process for the recovery of hydrocarbons from hydrocarbon containing materials, that includes the steps of: introducing the materials into a washing zone; introducing a solvent into the washing zone; agitating the materials and solvent to dissolve the hydrocarbons to form a hydrocarbon/solvent mixture; vaporizing the solvent in the hydrocarbon/solvent mixture; and recovering the hydrocarbons.

Additional objects of the invention are attained by a process for treating asphalt roofing materials to recover asphalt and solid components, including felt and granular materials, that includes the steps of: introducing the roofing materials and a solvent into a washing zone; agitating the roofing materials and solvent to form a solvent/asphalt mixture and separate the solid components from the asphalt; washing the granular materials in a solvent to remove any residual asphalt; heating the granular materials at a pressure below atmospheric pressure to dry the granular materials; heating the felt materials at a pressure below atmospheric pressure to dry the felt materials; heating the asphalt/solvent mixture to vaporize the solvent; recovering the solvent as a liquid by condensing the solvent vapor; and recovering the asphalt.

In one version of the process, the solvent is a terpene hydrocarbon. Monocyclic terpenes having the formula $C_{10}H_{16}$, including menthene, carvomethene, terpinene, phellandrene, limonene, terpinolene, camphene, carene, and pinene, are suitable solvents for use in the process of the invention. Monocyclic terpenes having the formula $C_{10}H_{20}$, including menthane, are also suitable solvents. The terpene hydrocarbons are an especially advantageous solvent when used in the process of the present invention as terpenes are natural, non-toxic, non-hazardous, biodegradable, and have a higher flash point than other solvents used in asphalt extraction. In addition, the terpenes can be removed from the asphalt without adversely affecting the chemical and physical properties of the asphalt. In another version of the process, the solvent is para-chlorobenzotriflouride, $ClC_6H_4CF_3$, which has proven to be effective in the solvent extraction step of the process of the invention. The para-chlorobenzotriflouride solvent is an advantageous solvent choice for the present invention as it does not have the environmental problems associated with other chlorinated solvents that are known ozone depleting agents or classified as Volatile Organic Compounds.

The process of the invention operates as a closed system at a pressure below atmospheric pressure, preferably at a vacuum pressure between 18 and 27.5 inches of mercury (60,783–92,863 pascals), to prevent the loss of solvent and maintain the quality of the environment around the system by limiting harmful emissions.

In accordance with another aspect of the invention, the foregoing objects and advantages of the present invention are attained by an apparatus for the recovery of hydrocarbons from hydrocarbon containing composite materials, that comprises: a composite materials washer for holding the hydrocarbon containing materials and a solvent; means for agitating the composite materials washer to dissolve the hydrocarbons forming a hydrocarbon/solvent mixture; a separator, in communication with the composite materials washer for vaporizing the solvent in the hydrocarbon/solvent mixture and recovering the hydrocarbons.

Additional objects of the invention are attained by an apparatus for the treatment of asphalt roofing materials to recover asphalt and the solid components, including felt and granular materials, that includes: a composite materials washer, a means for agitating the composite materials washer, a granular materials washer, a granular materials dryer, a felt materials dryer, a separator, a condenser, and means for recirculating the solvent within the apparatus.

The composite materials washer holds the roofing materials and a solvent, which are agitated by suitable means to form an asphalt/solvent mixture and to separate the solid components from the asphalt. The granular materials from the composite materials washer are transferred to the granular materials washer, wherein residual asphalt is removed from the granular materials by a solvent. The granular materials are then transferred to the granular materials dryer, wherein the granular materials are heated at a pressure below atmospheric pressure to dry the materials. The felt materials from the composite materials washer are transferred to the felt materials dryer and heated at a pressure below atmospheric pressure to dry the felt materials. The separator is used to vaporize the solvent in the asphalt/solvent mixture that is transferred from the composite materials washer. The condenser receives the vaporized solvent from the separator and recovers the solvent as a liquid. The recovered liquid solvent is recirculated to the composite materials washer and the granular materials washer by suitable means.

In another version of the apparatus of the invention, a granular materials classifier is connected to the granular materials dryer. The classifier separates the dried granular materials by particle size.

In still another version of the apparatus, the solid materials enter and exit the apparatus through air locks, and a vacuum generator maintains a system pressure below atmospheric pressure within the air locks. In a preferred version of the apparatus, the system pressure is maintained at a vacuum pressure between 18 and 27.5 inches of mercury (60,783–92,863 pascals). The combination of air locks and reduced pressure within this version of the apparatus minimizes the loss of solvent vapor and maintains the quality of the environment around the apparatus.

Solvents usable in the apparatus of the present invention include the terpene hydrocarbons. Monocyclic terpenes having the formula $C_{10}H_{16}$, including menthene, carvomethene, terpinene, phellandrene, limonene, terpinolene, camphene, carene, and pinene, are suitable solvents for use in the apparatus as well as monocyclic terpenes having the formula $C_{10}H_{20}$, including menthane. Another solvent, para-chlorobenzotriflouride, $ClC_6H_4CF_3$, has also proven to be effective in the apparatus of the invention.

The material flow of the process and apparatus of the present invention follows the following general path. Materials enter and exit the system through air locks. A negative pressure, i.e., a gauge pressure that is below atmospheric pressure, preferably a vacuum pressure between 18 and 27.5 inches of mercury (60,783–92,863 pascals), is maintained within the apparatus contained within the air locks to minimize solvent vapor losses.

The hydrocarbon containing composite material passes through the initial air lock to a non-heated composite materials washer. While the process will work with many solvents, the wash liquid in the preferred embodiment, is a non-hazardous, non-toxic, non-flammable, biodegradable terpene solvent, with a basic structure of $C_{10}H_{16}$ or $C_{10}H_{20}$. It is contemplated that both acyclic and cyclic terpenes are usable in the present invention, as well as terpene derivatives. In addition, many states may not consider this type of solvent a Volatile Organic Compound (VOC) due to its low vapor pressure. This is a significant feature as other processes to date use steam heat with hazardous, toxic, flammable, and non-biodegradable heptane or similar solvents. The process of the present invention relies on the solvent and agitating action of the washer to break down the composite material into its component parts.

After separation from the composite materials during the composite materials wash cycle, the granular material is passed through a gate to a granular materials washer where the granular material is washed in the solvent. The solvent, containing some dissolved hydrocarbons, is transferred to the composite materials washer where it is used to dissolve more hydrocarbons before being pumped back to the separator. This feature provides a significant advance in the art as other processes to date use steam heat with hazardous, toxic, flammable, and nonbiodegradable heptane or similar solvents.

The granular material then passes from the granular materials washer through an isolation feeder to a granular materials dryer where heat is applied to dry the granules. The dried granules then exit the system through an air lock to be recycled. The vaporized solvent from the granular materials dryer is then pumped through a condenser and transferred to the solvent storage tank to be reused.

After the granular material and the asphalt have been removed from the composite roofing material in the composite roofing materials wash cycle, the parent or felt material is transferred to a felt materials dryer where heat is applied to dry the felt material. The dried felt material then exits the system through an air lock to be recycled. The vaporized solvent from the felt materials dryer is then pumped through a condenser and transferred to the solvent storage tank to be reused.

The hydrocarbons that have been dissolved in the solvent in the composite materials washer are transferred to a solvent/hydrocarbon holding tank. The solvent/hydrocarbon mixture is then transferred to a separator, wherein the mixture is heated to vaporize the solvent. The hydrocarbons then exit the system to be recycled. The vaporized solvent from the separation process is then pumped through a condenser and transferred to the solvent storage tank to be reused.

A vacuum generator keeps a negative pressure, preferably a vacuum pressure between 18 and 27.5 inches of mercury (60,783–92,863 pascals), in the system contained within the air locks. This prevents loss of solvent and maintains the quality of the environment around the system.

Therefore, the process and apparatus of the present invention provide for cost effective solutions to the problem of recovering hydrocarbons from hydrocarbon containing materials without the need for hazardous solvents, grinding of the raw materials, introduction of water into the system, extensive solvent storage and recovery equipment, multiple washings with solvent, or the emission of harmful vapors to the environment.

The present invention also provides for a significant reduction in asphalt roofing material waste, a potentially special or hazardous waste that is rapidly filling our landfills. In addition, it will help many states to achieve and possibly exceed their targeted landfill waste reductions.

The above summarized description of the process and apparatus of the present invention shows that the present invention is a simplified cost effective way of recycling composite materials with a hydrocarbon or hydrocarbon derived binder, especially roofing materials comprised of asphalt, granular materials, and felt (glass fiber or organic). The process is not limited to the above mentioned materials and may include hydrocarbon derived binders and other components such as plastics, rubber, and other composite materials. It is particularly intended for roofing shingle tabs that are the byproducts of asphalt roofing shingle manufacture. It is directly applicable to other products such as roll roofing and shingles, although the addition of cutting and chopping equipment prior to the first above mentioned air lock may be economically justified in specific cases for optimal efficiencies. The present invention solves the problem of the disposal of asphalt roofing materials; as in some states, asphalt based materials, such as roofing products, are unacceptable in the landfills.

BRIEF DESCRIPTION OF THE DRAWINGS

These and other features, aspects, and advantages of the present invention will become better understood with regard to the following illustrative description, appended claims, and accompanying drawings where:

FIG. 1 is a schematic flow diagram of the present invention showing the composite materials washer used in separating the asphalt and solid components, the granular materials washer, the granular materials dryer and the granular materials classifier (screener), the parent (felt) materials dryer, and other auxiliary equipment used in the solvent extraction and solids reclamation portion of the present invention;

FIG. 2 is a schematic flow diagram of the remaining portion of the present invention showing the solvent/asphalt separator, the condenser (solvent reclaim and cooling unit), the solvent storage unit and recirculating pump, and other auxiliary equipment used in reclaiming the asphalt and solvent.

DETAILED DESCRIPTION OF THE INVENTION

Referring to FIG. 1, one version of the apparatus of the invention is shown wherein dry asphalt shingle tabs enter a processing system (01) via a hopper (10). The hopper (10) is simply a directional control device on the end of the user's conveyor where dry asphalt shingle tabs are being conveyed away from a shingle cutting operation.

The tabs pass from the hopper (10) through a composite materials entry air lock (12). Air that enters the upper half of the composite materials entry air lock (12) and vapors that come up through the bottom half of the composite materials entry air lock (12) are drawn off through a vacuum generator (32).

As the dry asphalt shingle tabs pass through the composite materials entry air lock (12), they subsequently enter a composite roofing materials washer (14). Once inside the composite roofing materials washer (14), the dry asphalt shingle tabs come in intimate contact with a solvent. As previously mentioned, while the process and apparatus will work with many solvents, the preferred embodiment is a non-hazardous, non-toxic, nonflammable and biodegradable terpene solvent with a basic structure of $C_{10}H_{16}$ or $C_{10}H_{20}$. The roofing materials washer (14) is agitated by suitable means, such as a drive assembly (not shown), to dissolve the asphalt in the solvent forming an asphalt/solvent mixture and to separate the solid components from the asphalt.

Once the granules are freed from the composite roofing material, the granules leave the composite roofing materials washer (14) by gravity flow through sliding gate valves (16) to a granular materials washer (18) where residual asphalt is dissolved and removed from the granular materials. The solvent from the granular materials washer (18), now containing dissolved asphalt (hereinafter the "solvent/asphalt liquid"), is transferred by a wash solvent supply pump (20) to the composite roofing materials washer (14), where more asphalt is dissolved.

The granules, now virtually free of asphalt, are dropped through a granules wash separation feeder (18B) and into a granular materials dryer (22) where the granular materials are heated at a pressure below atmospheric pressure. The combination of negative pressure and the addition of heat dries the granular materials and vaporizes any solvent. The vaporized solvent is transferred to a solvent reclaim, or condenser, (40), as shown in FIG. 2, wherein the solvent is recovered by condensing the vapor to the liquid phase.

Referring back to FIG. 1, the granules fall out of the processing system (01) through a granules exit air lock (24) into a granules, filler & sand screener, or classifier (26) where the granules are separated by particle size to be recycled.

The clean felt material, now being the original composite material less the granules and asphalt materials previously removed, drops out through the composite materials wash separation feeder (14B) into a felt, or parent, materials dryer (28) where the felt materials are heated at a pressure below atmospheric pressure. The combination of negative pressure and the addition of heat vaporizes any solvent and dries the felt material, which exits through a parent material exit air lock (30) to be recycled. The vaporized solvent is transferred to a solvent reclaim, or condenser (40), as shown in FIG. 2, wherein the solvent is recovered by condensing the vapor to the liquid phase. The felt materials dryer (28) is an existing state of the art dryer and is not claimed as inventive in itself in the present invention.

The solvent/asphalt liquid, as it overflows into the composite roofing materials washer (14), is transferred by a wash overflow return pump (34) through a solvent/asphalt surge tank prefilter (36A) and into a solvent/asphalt surge tank (36), as shown in FIG. 2.

Referring to FIG. 2, the solvent/asphalt liquid is pumped by a solvent/asphalt pump (37) through a solvent/asphalt preheater (38A) and into a solvent/asphalt separator (38) which separates the solvent from the asphalt by vaporizing the solvent. The flow of solvent/asphalt liquid into the solvent/asphalt separator (38) is controlled by means of a solvent/asphalt separator control valve (38B). In one embodiment of the invention, this would be a steam heated separator, but other methods obvious to those skilled in the state of the art would serve the same purpose. The solvent, which is a vapor at this point, then is pumped by a solvent reclaim pump (50) to a solvent reclaim, or condenser, (40) which cools the solvent vapor down to the liquid phase by means of a cooling unit (48).

The condensed liquid solvent, still under pressure, will be taken from the solvent reclaim, or condenser, (40) and stored at a solvent storage (44). The recycled solvent is distributed back into the system by a recirculating means, such as a granules wash solvent supply pump (42). By reclaiming the solvent and recirculating the recovered solvent to the composite roofing materials washer (14) and the granular materials washer (18), the invention can operate as a closed system, without the need for continual additions of fresh solvent. In this manner, the solvent introduced into the roofing materials washer (14) and the granular materials washer (18) consists of solvent from the solvent storage (44). Furthermore, the operation of the invention within air locks at a pressure below atmospheric pressure limits solvent vapor losses.

Referring to FIG. 1, the flow of the solvent into the composite roofing materials washer (14) is controlled by a composite material wash control valve (14A) and solvent flow into the granular materials washer (18) is controlled by a granules wash control valve (18A).

In operation, the invention produces the following process steps. The roofing materials are introduced into the roofing materials washer. A solvent is then introduced into the roofing materials washer. In one version of the invention, the solvent is a non-hazardous, non-flammable, non-toxic, biodegradable terpene solvent having the general formula $C_{10}H_{16}$ $C_{10}H_{20}$. The roofing materials and solvent are agitated to dissolve the asphalt in the solvent forming an asphalt/solvent mixture and to separate the solid components from the asphalt.

The granular materials from the roofing materials washer are transferred to the granular materials washer wherein the granular materials are washed in a solvent to remove any residual asphalt. The granular materials are then transferred to a granular materials dryer where the granular materials are heated at a pressure below atmospheric pressure to dry the granular materials. The granular materials are then transferred to a granular materials classifier where the granular materials are separated by particle size. The felt materials in the roofing materials washer are transferred to a felt materials dryer where the felt materials are heated at a pressure below atmospheric pressure to dry the felt materials.

The asphalt/solvent mixture from the roofing materials washer is transferred to a separator. The mixture is heated in the separator to vaporize the solvent. The asphalt is recovered, and the vaporized solvent from the separator and the solvent vapor produced when heating the granular and felt materials are transferred to a condenser where the solvent vapor is recovered as a liquid. The recovered liquid phase solvent is then transferred to a solvent storage zone. The solvent from the solvent storage is then recirculated to the roofing materials washer and the granular materials washer. The process steps are advantageously executed within a closed system maintained at a pressure below atmospheric pressure, preferably at a vacuum pressure between 18 and 27.5 inches of mercury (60,783–92,863 pascals).

Asphalt shingle tabs were selected as the waste materials used to illustrate the present invention in the detailed description included hereinabove. However, the process equipment of the present invention can be sized to handle larger particles, such as entire asphalt roofing shingles or, as an alternative to sizing for larger pieces of material, conventional methods and equipment can be used to chop the material to be processed into appropriately sized pieces prior to entering the composite materials entry air lock (12).

The specific process and apparatus described herein is applicable to other hydrocarbon or hydrocarbon derived composite materials. The asphalt shingle tabs have been used herein as an illustrative example. Although the foregoing description contains many specificities, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A continuous process for the recovery of hydrocarbons from hydrocarbon containing composite materials selected from roofing materials and byproducts thereof, said process executed within a closed system maintained below atmospheric pressure and including the steps of:

introducing the materials into a washing zone;

introducing a solvent into the washing zone;

agitating the materials and solvent to dissolve the hydrocarbons to form a hydrocarbon/solvent mixture;

vaporizing the solvent in the hydrocarbon/solvent mixture; and recovering the hydrocarbons.

2. The process according to claim 1 wherein the solvent is a terpene.

3. The process according to claim 2 wherein the terpene is selected from the group consisting of menthene, carvomethene, terpinene, phellandrene, limonene, terpinolene, camphene, carene, pinene and menthane.

4. The process according to claim 1 wherein the solvent is para-chlorobenzotriflouride.

5. The process according to claim 1 further including the step of condensing the vaporized solvent to recover the solvent as a liquid.

6. The process according to claim 5 further including the step of recirculating the recovered liquid solvent to the washing zone.

7. The process according to claim 1 wherein the hydrocarbon containing materials are roofing materials including felt and granular materials and the hydrocarbons are asphalt.

8. The process according to claim 7 wherein the roofing materials are introduced whole into the washing zone.

9. The process according to claim 7 wherein the felt and granular materials are separately recovered and treated to recover the solvent contained therein.

10. The process according to according to claim 1 wherein the closed system operates at a vacuum pressure between 18 and 27.5 inches of mercury (60,783–92,863 pascals).

11. An apparatus for the recovery of hydrocarbons from hydrocarbon containing composite material selected from roofing materials and byproducts thereof said apparatus comprising:

a composite materials washer holding the hydrocarbon containing materials and a solvent;

means for agitating the composite materials washer to dissolve the hydrocarbons forming a hydrocarbon/solvent mixture;

a separator, in communication with the composite materials washer, for vaporizing the solvent in the hydrocarbon/solvent mixture and recovering the hydrocarbons; and means for maintaining the apparatus below atmospheric pressure.

12. The apparatus according to claim 11 further comprising:

a condenser, in communication with the separator, for recovering as a liquid the solvent vapor from the separator; and means for recirculating the solvent recovered in the condenser to the composite materials washer.

13. The apparatus according to claim 11 wherein the hydrocarbon containing composite materials are roofing materials including felt and granular materials and the hydrocarbons are asphalt.

14. The apparatus according to claim 13 further comprising:

a granular materials washer, in communication with the composite materials washer, for removing residual asphalt from the granular materials transferred from the composite materials washer;

a granular materials dryer, in communication with the granular materials washer, for heating the granular materials transferred from the granular materials washer, to dry the granular materials; and a felt materials dryer, in communication with the composite materials washer, for heating the felt materials transferred from the composite materials washer, to dry the felt materials.

15. The apparatus according to claim 14 wherein the granular materials dryer and the felt materials dryer are in communication with the condenser, the solvent vapor produced during the heating of the granular and felt materials being transferred to the condenser for recovery as a liquid.

16. The apparatus according to claim 14 further comprising:

a granular materials classifier, in communication with the granular materials dryer, for separating the granular materials by particle size after drying.

17. The apparatus according to claim 14 wherein said means for maintaining the apparatus below atmospheric pressure includes a plurality of air locks whereby the composite materials enter the composite materials washer through an air lock, the granular materials exit the granular materials dryer through an air lock, and the felt materials exit the felt materials dryer through an air lock.

18. The apparatus according to claim 17 further comprising:

a vacuum generator for maintaining a system pressure below atmospheric pressure within the air locks.

19. The apparatus according to claim 18 wherein the system pressure is maintained at a vacuum pressure between 18 and 27.5 inches of mercury (60,783–92,863 pascals).

20. The apparatus according to claim 11 wherein the solvent is a terpene.

21. The apparatus according to claim 20 wherein the terpene is selected from the group consisting of menthene, carvomethene, terpinene, phellandrene, limonene, terpinolene, camphene, carene, pinene and menthane.

22. The apparatus according to claim 11 wherein the solvent is para-chlorobenzotriflouride.

* * * * *